(12) United States Patent
Yamanishi et al.

(10) Patent No.: US 8,038,860 B2
(45) Date of Patent: *Oct. 18, 2011

(54) BIOSENSOR

(75) Inventors: Eriko Yamanishi, Ehime (JP); Hiroyuki Tokunaga, Ehime (JP); Akihisa Higashihara, Ehime (JP)

(73) Assignee: Panasonic Corporation, Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/908,233

(22) Filed: Oct. 20, 2010

(65) Prior Publication Data

US 2011/0036713 A1    Feb. 17, 2011

Related U.S. Application Data

(62) Division of application No. 11/993,782, filed as application No. PCT/JP2006/312665 on Jun. 23, 2006.

(30) Foreign Application Priority Data

Jun. 24, 2005  (JP) .................................. 2005-184306

(51) Int. Cl.
*G01N 27/327* (2006.01)
*G01N 27/26* (2006.01)
(52) U.S. Cl. ......... 204/403.04; 204/403.01; 204/403.14; 204/403.11
(58) Field of Classification Search ..... 204/400–403.15; 205/775, 777.5, 778, 792; 422/401, 402, 422/408, 412, 419
See application file for complete search history.

(56) References Cited

U.S. PATENT DOCUMENTS

| | | | |
|---|---|---|---|
| 5,437,999 A | 8/1995 | Diebold et al. | |
| 5,512,159 A | 4/1996 | Yoshioka et al. | |
| 6,977,032 B2 | 12/2005 | Hasegawa et al. | |
| 7,070,680 B2 * | 7/2006 | Bae et al. | 204/403.04 |
| 2002/0134676 A1 | 9/2002 | Watanabe et al. | |
| 2003/0028125 A1 | 2/2003 | Yuzhakov et al. | |
| 2003/0159945 A1 | 8/2003 | Miyazaki et al. | |
| 2003/0196894 A1 | 10/2003 | Cai et al. | |
| 2005/0194251 A1 | 9/2005 | Miyazaki et al. | |
| 2005/0239194 A1 | 10/2005 | Takahashi et al. | |

FOREIGN PATENT DOCUMENTS

| | | |
|---|---|---|
| JP | 2002-168821 | 6/2002 |
| JP | 2003-116821 | 4/2003 |
| JP | 2005-43122 | 2/2005 |

OTHER PUBLICATIONS

International Search Report issued Jul. 25, 2006 in the International (PCT) Application No. PCT/JP2006/312665.
Written Opinion of the ISA issued Jul. 25, 2005 in the International (PCT) Application No. PCT/JP2006/312665.
Office Action issued Dec. 23, 2010 in corresponding U.S. Appl. No. 11/993,782.

* cited by examiner

*Primary Examiner* — Jeffrey T Barton
*Assistant Examiner* — Jennifer Dieterle
(74) *Attorney, Agent, or Firm* — Wenderoth, Lind & Ponack, L.L.P.

(57) ABSTRACT

A biosensor can supply a sample solution accurately and easily, and includes a capillary for collecting a sample solution and analyzes a specific substance in the sample solution, an air hole, and at least two supply ports, i.e., a sample supply port and an auxiliary sample supply port, so that supply of the sample solution can be performed from either of the supply ports. Even when the sample supply port is closed up with a fingertip or the like and supply of the sample solution is stopped, the sample solution can be quickly supplied from the other auxiliary sample supply port.

15 Claims, 10 Drawing Sheets

BIOSENSOR

This application is a Divisional of U.S. application Ser. No. 11/993,782, filed Dec. 21, 2007, which is a national stage application of International application No. PCT/JP2006/312665, filed Jun. 23, 2006.

TECHNICAL FIELD

The present invention relates to a biosensor for analyzing a specific component in a sample solution, and more particularly, to a biosensor which collects a small amount of sample solution by capillary phenomenon onto a small-size test specimen, and analyzes the sample solution.

BACKGROUND ART

A biosensor is a sensor for determining a quantity of a base substance in a sample solution, which utilizes a molecule recognizing ability of a biological material such as microorganism, enzyme, antibody, DNA, RNA or the like to employ the biological material as a molecule discrimination element. To be specific, the biosensor determines a quantity of a base substance contained in a sample solution by utilizing a reaction which occurs when a biological material recognizes an objective substrate, such as consumption of oxygen due to respiration of a micro-organism, enzyme reaction, light emission, and the like. Among various kinds of biosensors, an enzyme sensor has come into practical use. For example, an enzyme sensor as a biosensor for glucose, lactic acid, cholesterol, or amino acid has been utilized for medical analysis and food industry. In this enzyme sensor, an electron carrier is reduced by electrons that are generated due to a reaction between a base substance included in a sample solution as an analyte and enzyme or the like, and a measurement unit electrochemically measures a reduction quantity of the electron carrier, thereby performing quantitative analysis for the sample.

There have been proposed various types of biosensors. For example, as a biosensor that facilitates measurement of a blood glucose level, there is a biosensor comprising a first insulating substrate on which a pair of electrodes and a reagent layer are formed, a second insulating substrate bonded to the first insulating substrate via a spacer, and a capillary for collecting a sample solution, which is provided between the both insulating substrates. The biosensor is constituted such that blood obtained by puncturing the human body is introduced by capillary phenomenon into the capillary from a sample supply port that opens at one ends of the both substrates.

In this biosensor, however, there is a possibility that the blood is not successfully introduced into the capillary depending on the angle of the biosensor when the blood is applied onto the sample supply port, and thereby the blood might be attached to the outer surface of the insulating substrate by mistake. In this case, even when the user tries to supply the blood again, the blood attached to the outer surface impedes the user from successfully supplying the blood into the capillary, resulting in faulty measurement and measurement errors.

In order to solve this problem, the inventors of the present invention have proposed a biosensor in which the ends of the both substrates which constitute the sample supply port are formed in different shapes when viewed planarly so that blood can always be introduced into the capillary successfully without being influenced by the angle of the biosensor when the blood is applied (refer to Patent Document 1).

FIG. 8 illustrates an exploded perspective view and a cross-sectional view of the biosensor disclosed in Patent Document 1. In FIG. 8, reference numeral 1 denotes a first insulating substrate, and a measurement electrode 2, a counter electrode 3, and a detector electrode 4, which comprise an electric conducting material, are formed on the first insulating substrate 1.

The conventional biosensor 800 is formed by bonding the first insulating substrate 1, a spacer 6, and a second insulating substrate 8 together, and a capillary 7 is formed by the existence of a notch in the spacer 6. A test sample is introduced into the capillary 7 from its front end by a sample supply port 13 that is formed by the bonding and an air hole 9 formed through the insulating substrate 1.

Further, the measurement electrode 2, the counter electrode 3, and the detector electrode 4 which are formed on the first insulating substrate 1 are exposed in the capillary 7, and a reagent layer 5 is formed in a position opposed to these electrodes.

A measurement instrument (not shown) having terminals to be connected to leads 10, 11, and 12 of the electrodes is inserted in the biosensor before introduction of blood, and variation in the electric characteristics which occurs due to a reaction of the blood with the reagent is detected between the measurement electrode 2 and the counter electrode 3 after introduction of blood, thereby measuring a glucose concentration.

Patent Document 1: Japanese Published Patent Application No. 2002-168821).

DISCLOSURE OF THE INVENTION

Problems to be Solved by the Invention

In blood glucose measurement in recent years, it is desired to minimize the quantity of blood to be collected in order to reduce pain of a diabetic patient as much as possible. Therefore, development of a biosensor in which the size of the capillary for collecting blood and the size of the sample supply port are further reduced has been progressed.

However, such miniaturization in the conventional biosensor has caused a problem that the sample supply port is easily closed up when a deformable object such as a finger chip is pressed thereto.

FIG. 9 shows a state where blood is aspirated in the conventional biosensor.

As shown in FIG. 9(a), when the sample supply port 13 is closed up by a fingertip, supply of blood is interrupted, and the blood is not completely filled in the capillary 7 but stops in the middle of the capillary 7. Then, shortage of sample quantity occurs, which may prevent measurement, or display of incorrect results. Further, even when the capillary is completely filled with the blood by rightly separating the finger as shown in FIG. 9(b) after the finger has once closed the sample supply port 13, there occurs a difference in dissolution of the reagent layer due to the initially introduced blood, resulting in variations in measurement, and therefore, accurate measurement cannot be carried out.

Although it might be considered that the difference in the shapes between the first insulating substrate and the second insulating substrate may be further increased to prevent the fingertip from closing the sample supply port, this is a distant idea. The reason is as follows. If the difference in the shapes is increased too much, not only the blood stored inside the capillary but also the blood stored outside the capillary increases, and thus more blood is required.

The present invention is made to solve the above-described problems and has for its object to provide a biosensor having a construction that can reliably collect a sample solution into a capillary even when the quantity of the sample solution is very small.

Measures to Solve the Problems

In order to solve the above-mentioned problems, there is provided a biosensor which is formed by bonding a first insulating substrate and a second insulating substrate together, and comprises a sample supply port which opens at one end of the both substrates, to which a sample solution is applied, a capillary communicated with the sample supply port, into which the applied sample solution is introduced by capillary phenomenon, and an air hole which is positioned at an end of the capillary and communicated with air inside the capillary, the supply port, the capillary, and the air hole being formed by the bonding of the both insulating substrates, wherein at least one auxiliary sample supply port communicated with the capillary, through which the applied sample solution is introduced into the capillary, is provided in the vicinity of the sample supply port.

Further, the auxiliary sample supply port is obtained by forming a through-hole in the first insulating substrate or the second insulating substrate so as to leave a portion of the insulating substrate between the auxiliary sample supply portion and the sample supply port.

Further, a spacer having a groove to provide the sample supply port, the auxiliary sample supply port, and the capillary is disposed between the first insulating substrate and the second insulating substrate, and the auxiliary sample supply port is provided at the ends of the both substrates.

Effects of the Invention

According to the present invention, since a biosensor which has a capillary structure and performs measurement with a very small quantity of sample is constituted as described above, even when a sample supply port is closed up by elastic skin such as fingertip, brachial region, or abdominal region of a test subject, it is possible to perform reliable aspiration of the sample solution from an auxiliary sample supply port into the capillary.

DESCRIPTION OF THE REFERENCE NUMERALS

Figure 1A:
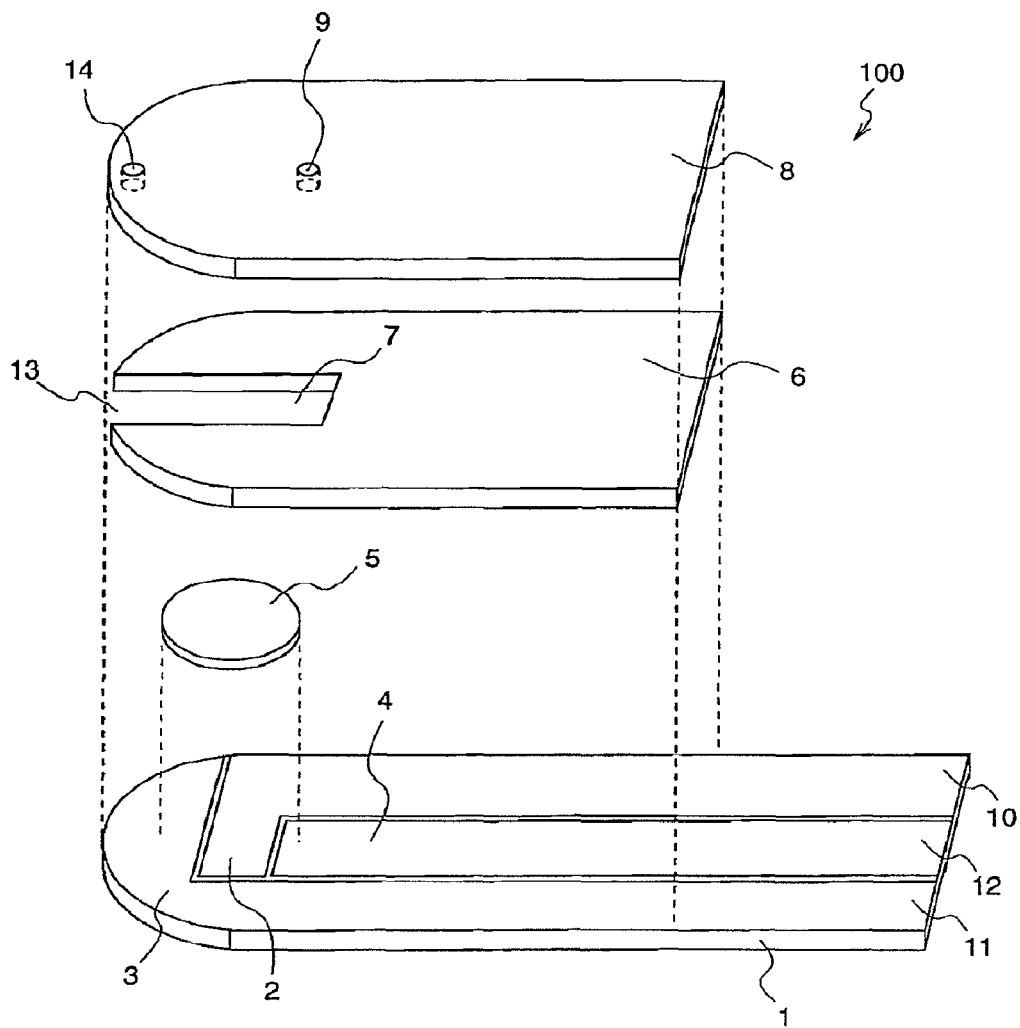
FIG. 1 illustrates an exploded perspective view and a cross-sectional view of a biosensor 100 according to a first embodiment of the present invention.

100 . . . biosensor
200 . . . biosensor
300 . . . biosensor
400 . . . biosensor
500 . . . biosensor
600 . . . biosensor
700 . . . biosensor
800 . . . biosensor
1 . . . first insulating substrate
2 . . . measurement electrode
3 . . . counter electrode
4 . . . detector electrode
5 . . . reagent layer
6 . . . spacer
7 . . . capillary
8 . . . second insulating substrate
9 . . . air hole
10 . . . lead
11 . . . lead
12 . . . lead
13 . . . sample supply port
14 . . . auxiliary sample supply port
15 . . . notch
16 . . . blood
17 . . . fingertip

DETAILED DESCRIPTION OF THE INVENTION

Hereinafter, embodiments of a biosensor according to the present invention will be described taking a blood glucose sensor as an example with reference to the drawings.

Embodiment 1

FIG. 1 illustrates an exploded perspective view and a cross-sectional view of a biosensor 100 according to a first embodiment of the present invention.

In the biosensor 100 shown in FIG. 1, reference numeral 1 denotes a first insulating substrate having a portion near a front end being formed approximately in a semicircular shape, and a portion that follows the front end to reach a rear end being formed in a rectangle. A measurement element 2, a counter electrode 3, and a detector electrode 4 which are composed of an electric conducting material are formed on the first insulating substrate 1. Reference numeral 8 denotes a second insulating substrate which is formed in a shape similar to that of the first insulating substrate 1, reference numeral 6 denotes a spacer which is disposed between the first insulating substrate 1 and the second insulating substrate 8 and is formed in a shape similar to those of the both insulating substrates, and reference numeral 7 denotes a capillary which is formed so as to form an approximately rectangle convex portion in the vicinity of the front end of the spacer, along the longitudinal direction of the spacer.

The biosensor 100 is formed by bonding the first insulating substrate 1, the spacer 6, and the second insulating substrate 8 together, and the capillary 7 is formed by existence of the above-mentioned notch in the spacer 6. A test sample is introduced into the capillary 7 by a sample supply port 13 that is formed by the bonding, and an air hole 9 that is provided through the first insulating substrate 1 in a position opposed to a rear end of the capillary 7.

Further, reference numerals 10, 11, and 12 denote leads of the measurement electrode 2, the counter electrode 3, and the detector electrode 4, respectively, which correspond to the rear end portions of the respective electrodes disposed on the first insulating substrate 1, and reference numeral 13 denotes a sample supply port which is formed by that a forward space portion of the capillary 7 is sandwiched by the first and second insulating substrates 1 and 8.

Further, the measurement electrode 2, the counter electrode 3, and the detector electrode 4 formed on the first insulating substrate 1 are exposed in the capillary 7, and a reagent layer 5 is disposed in a position opposed to these electrodes.

When performing measurement using the biosensor 100 of the first embodiment, variations in the electric characteristics between the measurement electrode 2 and the counter electrode 3 are detected with the biosensor 100 being inserted in a measurement instrument (not shown) having terminals which are to be connected to the leads 10, 11, and 12 of the respective electrodes 2, 3, and 4, thereby to analyze the characteristics of the test sample.

While the detector electrode 4 functions as an electrode for detecting a shortage in the quantity of the sample, it may be used as a reference electrode or a portion of the counter electrode.

While in FIG. 1 the respective electrodes 2, 3, and 4 are disposed on the first insulating substrate 1, these electrodes may be partially disposed on the opposed second insulating substrate 8 as well as on the first insulating substrate 1.

Preferable materials of the first insulating substrate 1, the spacer 6, and the second insulating substrate 8 include polyethylene terephthalate, polycarbonate, and polyimide. The thicknesses of the first and second insulating substrates are desired to be 0.1 to 5.0 mm.

Further, the electric conducting material constituting the respective electrodes 2, 3, and 4 may include a single substance such as a noble metal (gold, platinum, or palladium) or carbon, or a complex substrate such as carbon paste or a noble metal paste. Sputtering or the like is adopted for the former substance while screen printing or the like is adopted for the latter substance, thereby easily forming the electric conducting layer on the first insulating substrate 1 or the second insulating substrate 8.

Further, when forming the respective electrodes, initially an electric conducting layer is formed on the entire surface or a portion of the first insulating substrate 1 or the second insulating substrate 8 by the above-mentioned sputtering or screen printing, and then slits are formed in the electric conducting layer using a laser or the like, thereby fabricating the separated electrodes. Alternatively, the respective electrodes can be similarly produced by screen printing or sputtering using a print board or a mask board on which electrode patterns have already been formed.

The reagent layer 5 including enzyme, electron carrier, hydrophilic macromolecule, and the like is formed on the electrodes 2, 3, and 4. The enzyme may be any of glucose oxidase, lactate oxidase, cholesterol oxidase, cholesterol esterase, uricase, ascorbate oxidase, bilirubin oxidase, glucose dehydrogenase, and lactate dehydrogenase. The electron carrier may be any of potassium ferricyanide, p-benzoquinone and its derivative, phenazine methosulfate, methylene blue, and ferrocene and its derivative.

The hydrophilic macromolecule may be any of carboxymethyl cellulose, hydroxyethyl cellulose, hydroxypropyl cellulose, methyl cellulose, ethyl cellulose, ethylhydroxyethyl cellulose, carboxymethylethyl cellulose, polyvinyl alcohol, polyvinylpyrrolidone, polyamino acid such as polylysine, polystyrene sulfonate, gelatine and its derivative, acrylic acid and its salt, and agarose gel and its derivative.

Next, the capillary 7 to which blood is to be supplied is formed by bonding the first insulating substrate 1 and the second insulating substrate 8 with the spacer 6 between them. The sample supply port 13 through which the blood is to be introduced into the capillary 7 is opened at the ends of the first insulating substrate 1 and the second insulating substrate 8.

In this first embodiment, the thickness of the spacer 6 is 0.025 to 0.5 mm, the width of the capillary 7 is 0.1 to 10 mm, and the volume of the capillary 7 is 0.1 to 5 μL.

The construction of the first embodiment is characterized by that an auxiliary sample supply port 14 penetrating through the second insulating substrate 8 on the capillary 7 is provided. After this auxiliary sample supply port 14 is formed through the second insulating substrate 8, the second insulating substrate 8 is bonded to the first insulating substrate 1 and the spacer 6, thereby completing the biosensor.

Figure 10:
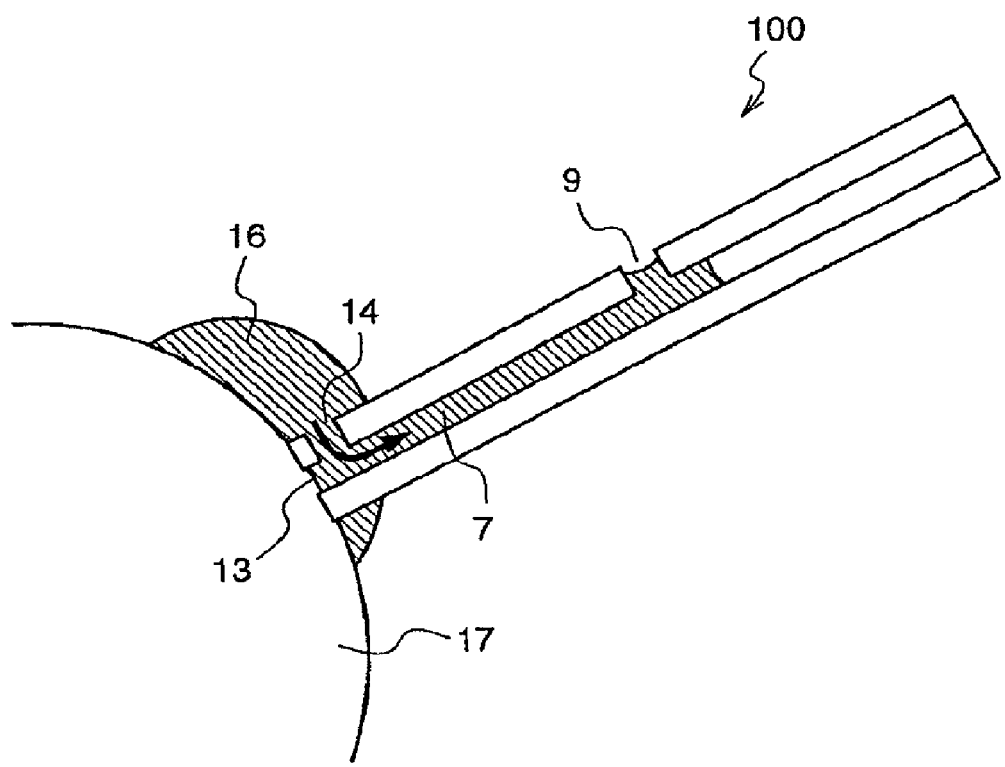
FIG. 10 is a cross-sectional view illustrating a state where blood is aspirated in the biosensor 100 according to the first embodiment.

Since the auxiliary sample supply port 14 is provided, even when the sample supply port 13 is closed up with a finger chip when applying the blood and thereby supply of the blood from the sample supply port 13 is blocked, the blood can be introduced into the capillary from the auxiliary sample supply port 14 provided through the second insulating substrate 8 as shown in FIG. 10, whereby the capillary 7 can be completely filled with the blood.

This auxiliary sample supply port 14 is desired to be provided in a position to which the sample solution is always attached when the sample solution is supplied. Hereinafter, a description will be given of the position, size, shape, and number of the auxiliary sample supply port 14.

Figure 1B:
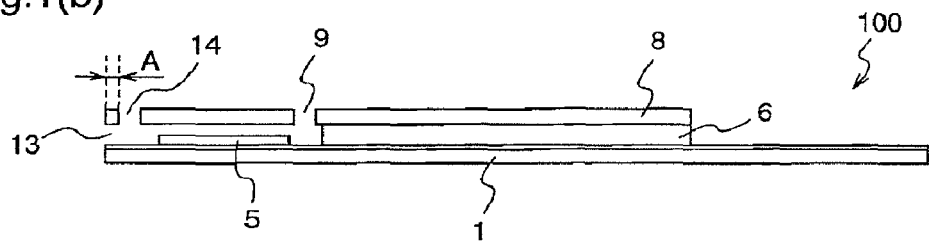

The distance between the sample supply port 13 and the auxiliary sample supply port 14, i.e., the size of A shown in the cross-sectional view of FIG. 1(b), is desirably at least 0.05 to 5.0 mm. When the distance is smaller than 0.05 mm, there is a possibility that the two supply ports might be connected and the effect as the auxiliary sample supply port is reduced. Further, in the recent biosensor which is desired to minimize the quantity of blood, if the distance is larger than 5.0 mm, it becomes difficult to apply the sample to the sample supply port 13 and to the auxiliary sample supply port 14 simultaneously.

The area of the auxiliary sample supply port 14 is desired to be 0.01 to 3.0 mm$^2$. When the area is smaller than 0.01 mm$^2$, the auxiliary sample supply port 14 lacks the ability of aspirating the sample solution, and thereby the supply speed is reduced or the supply is stopped halfway. When the area is larger than 3.0 mm$^2$, the size of the capillary must be increased, which leads to an increase in the quantity of the sample, and therefore, this is a distant idea.

It is desired to process the auxiliary sample supply port 14 using a laser. Although press cutting, die cutting, and Thomson cutting are also applicable for processing the supply port, laser processing is most preferable because it enables microfabrication.

A plurality of auxiliary sample supply ports 14 may be provided on the second insulating substrate 8, with favorable effects. Further, the shape of the auxiliary sample supply port 14 is not restricted to that mentioned above so long as the above-mentioned conditions are satisfied. For example, it may be circular, oval, linear, rectangular, triangular, or the like.

Further, while the auxiliary sample supply port 14 is provided on the second insulating substrate 8, it may be provided on the first insulating substrate 1. At this time, the position, shape, and size of the auxiliary sample supply port 14 are identical to those mentioned above.

Figure 2A:
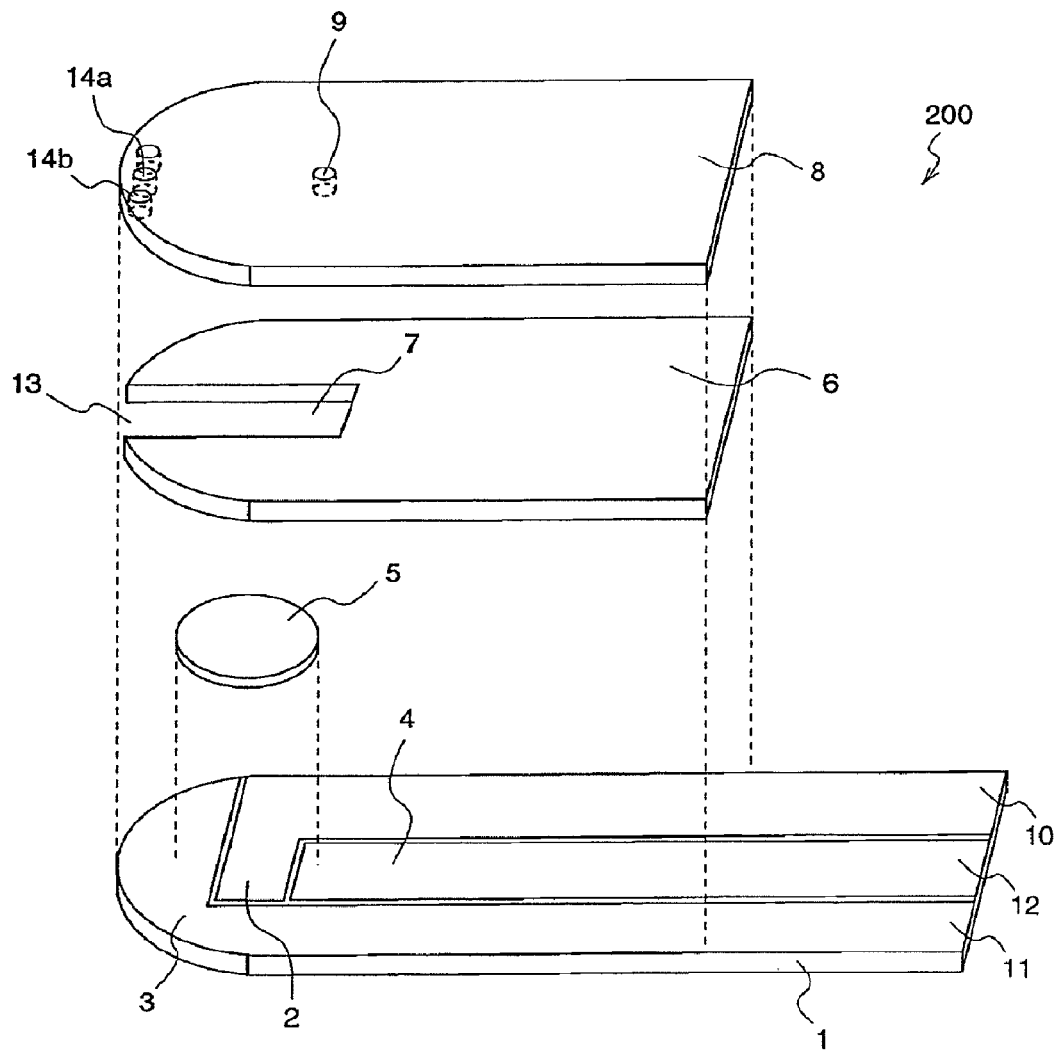
FIG. 2 illustrates an exploded perspective view and a cross-sectional view of a biosensor 200 according to a modification of the first embodiment.
Figure 2B:
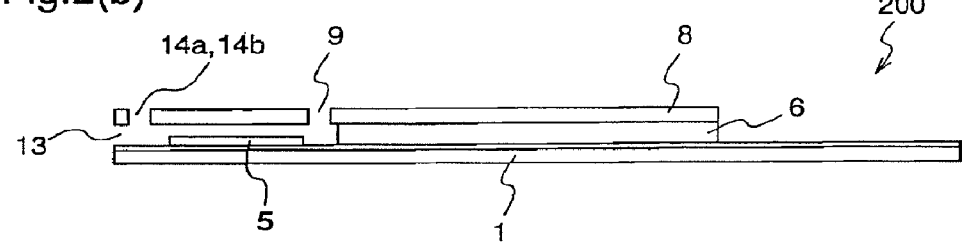
Figure 3A:
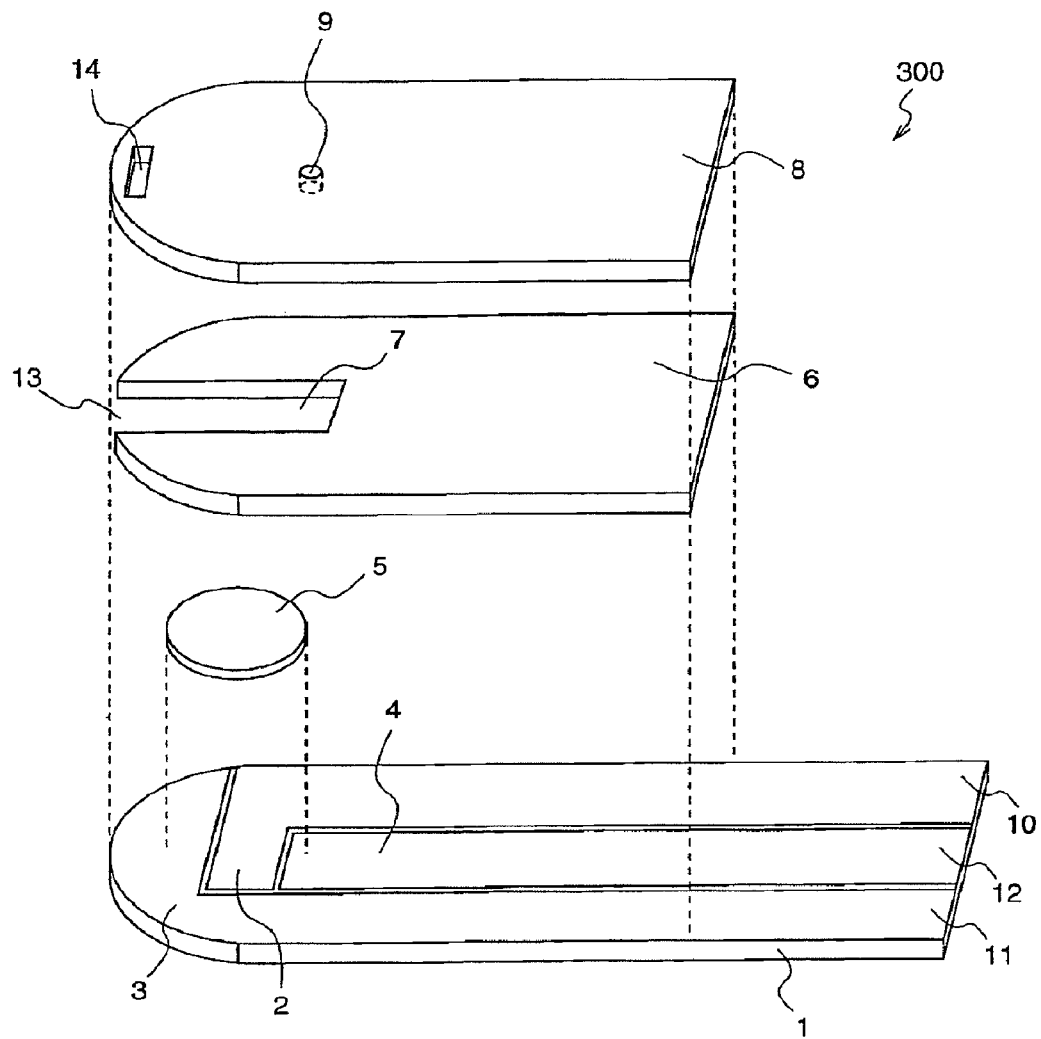
FIG. 3 illustrates an exploded perspective view and a cross-sectional view of a biosensor 300 according to another modification of the first embodiment.
Figure 3B:
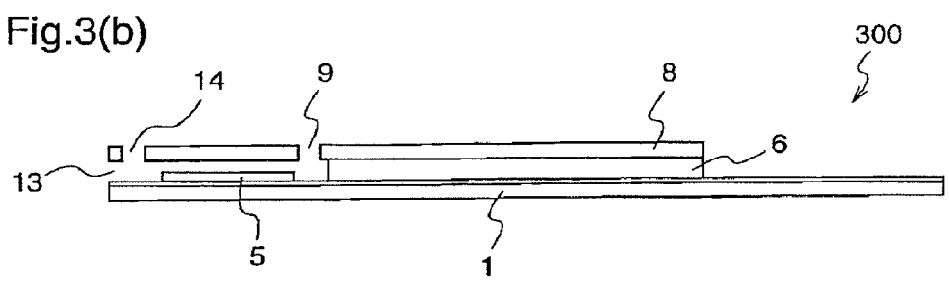

Further, the shape of the biosensor 100 is not restricted to that of the first embodiment shown in FIG. 1, and the same effects as mentioned above can be achieved even when the biosensor has a shape according to a modification shown in FIG. 2 or a shape according to another modification shown in FIG. 3.

To be specific, a biosensor 200 according to a modification of the first embodiment shown in FIG. 2 has plural auxiliary sample supply ports 14*a* and 14*b*.

Further, a biosensor 300 according to another modification of the first embodiment shown in FIG. 3 has a rectangular auxiliary sample supply port 14.

Figure 4A:
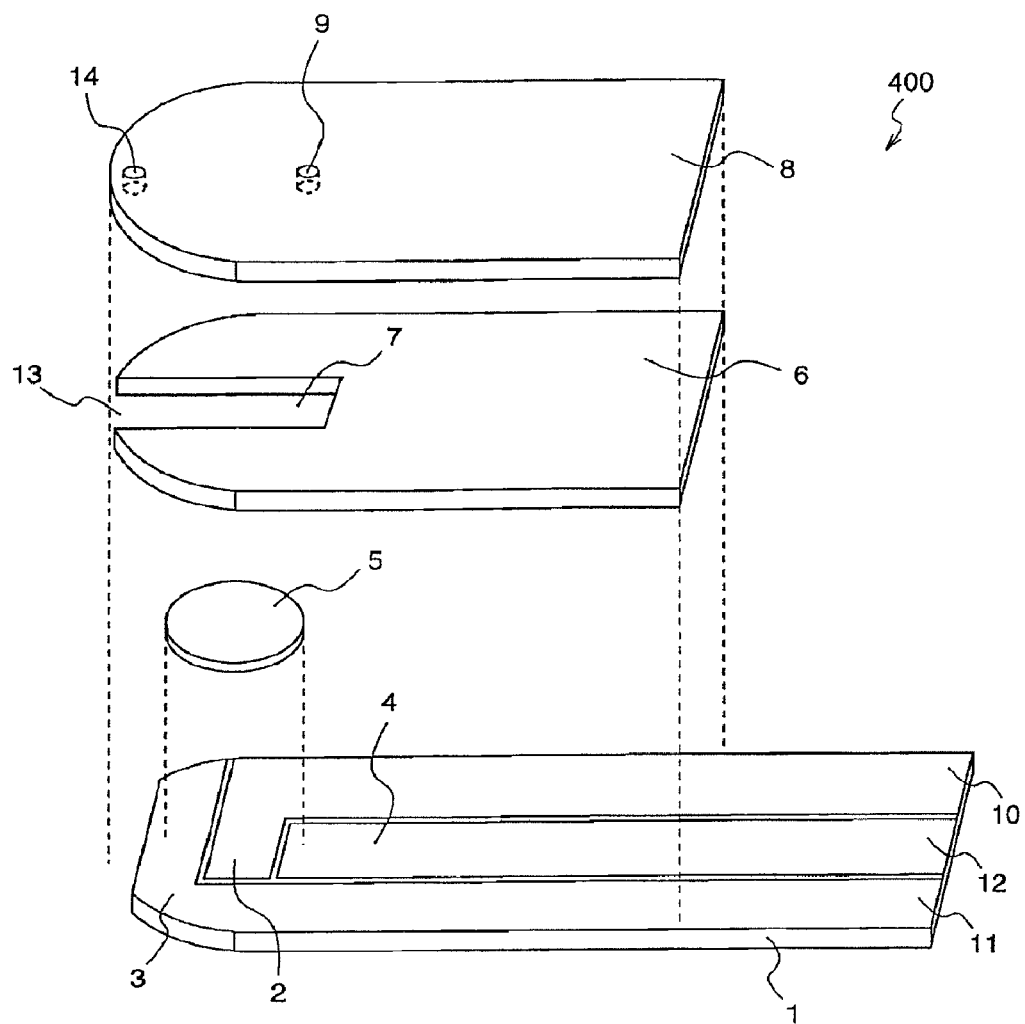
FIG. 4 illustrates an exploded perspective view and a cross-sectional view of a biosensor 400 according to still another modification of the first embodiment.
Figure 4B:
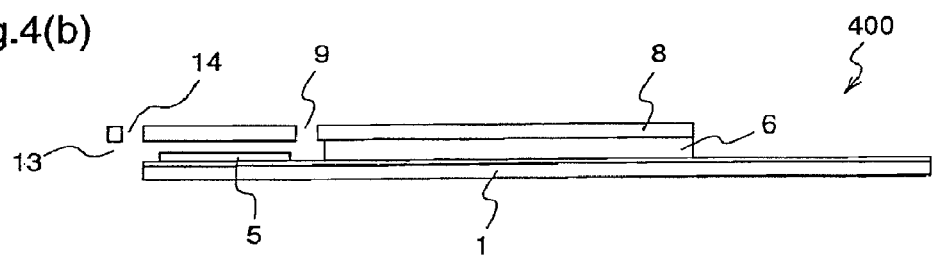

Furthermore, FIG. 4 shows a biosensor 400 according to still another modification of the first embodiment. This biosensor 400 is constituted such that the first insulating substrate 1 and the second insulating substrate 8 which form the capillary 7 are bonded together shifted from each other so that the end portions thereof viewed planarly are located in different positions.

That is, in FIG. 4, the second insulating substrate 8 and the spacer 6 are protruded by 0.1 to 1.0 mm toward the sample supply port 13 with respect to the first insulating substrate 1.

The biosensors 200, 300, and 400 shown in FIGS. 2, 3, and 4 also achieve the same effects as the biosensor 100 shown in FIG. 1.

When the electrodes 2, 3, and 4 and the reagent layer 5 for electrochemically analyzing a specific substance in the sample solution are provided inside the capillary 7, it is desired that these electrodes 2, 3, 4 and the reagent layer 5 are not disposed at a position on the first insulating substrate 1 directly beneath the auxiliary sample supply port 14.

If the auxiliary sample supply port 14 is disposed above the electrodes 2, 3, and 4, the sample solution on the electrodes is likely to vary, and this variation may cause undesirable variation in the response value.

The biosensors 200, 300, and 400 shown in FIGS. 2, 3, and 4 also achieve the same effects as the biosensor 100 shown in FIG. 1.

Further, in the above-mentioned biosensors 100, 200, 300, and 400, it is desired that a surface-activating treatment is applied to the entirety or a portion of the inner wall of the capillary 7. Thereby, even when the area of the sample supply port is small, the capillary can speedily aspirate the sample solution.

Further, it is desired that a surface-activating treatment is applied to the inner side of the auxiliary sample supply port 14, or the entire inner wall of the capillary, or a portion of the inner wall of the capillary in the vicinity of the auxiliary sample supply port.

When a surface-activating treatment is applied to the inner side of the auxiliary sample supply port 14 or the inner wall of the capillary, aspiration of the sample solution is quickly started as soon as the sample solution contacts the auxiliary sample supply port 14, and thereby the capillary is filled with the sample solution before the supply port is closed up by a fingertip or the like.

The surface-activating treatment includes coating of a non-ionic, cationic, anionic, or zwitterionic surfactant, corona discharge treatment, and physical processing to form fine concavities and convexities on the surface.

As described above, according to the biosensor of the first embodiment, even when the sample supply port 13 is closed up while the sample solution is being supplied, the sample solution is speedily supplied from the auxiliary sample supply port 14, and thereby the sample solution is aspirated into the capillary accurately and easily.

Embodiment 2

Figures 5A, 5B:
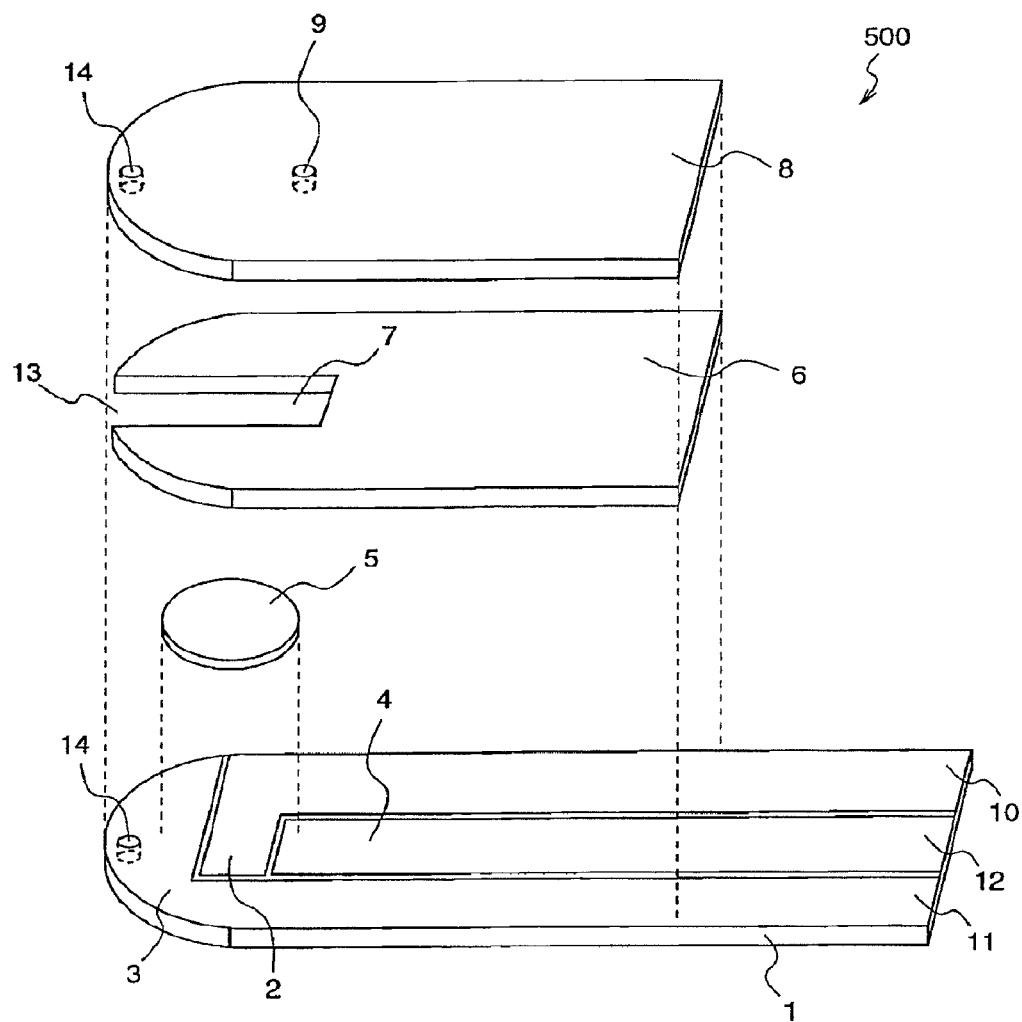
FIG. 5 illustrates an exploded perspective view and a cross-sectional view of a biosensor 500 according to a second embodiment of the present invention.

FIG. 5 illustrates an exploded perspective view and a cross-sectional view of a biosensor 500 according to a second embodiment of the present invention.

In the biosensor 500 of the second embodiment shown in FIG. 5, auxiliary sample supply ports 14 are provided on both the first insulating substrate 1 and the second insulating substrate 8.

Since the auxiliary sample supply ports 14 are provided on the two insulating substrates 1 and 8, respectively, even if the sample is applied from a biased angle, the sample can be reliably aspirated into the space 6.

Further, as described in the first embodiment, plural auxiliary sample supply ports 14 may be provided on the respective substrates with the same effects as mentioned above.

Further, the shape of the auxiliary sample supply port 14 is not particularly restricted, and it may be circular, oval, linear, rectangular, or triangular.

Embodiment 3

Figure 6A:
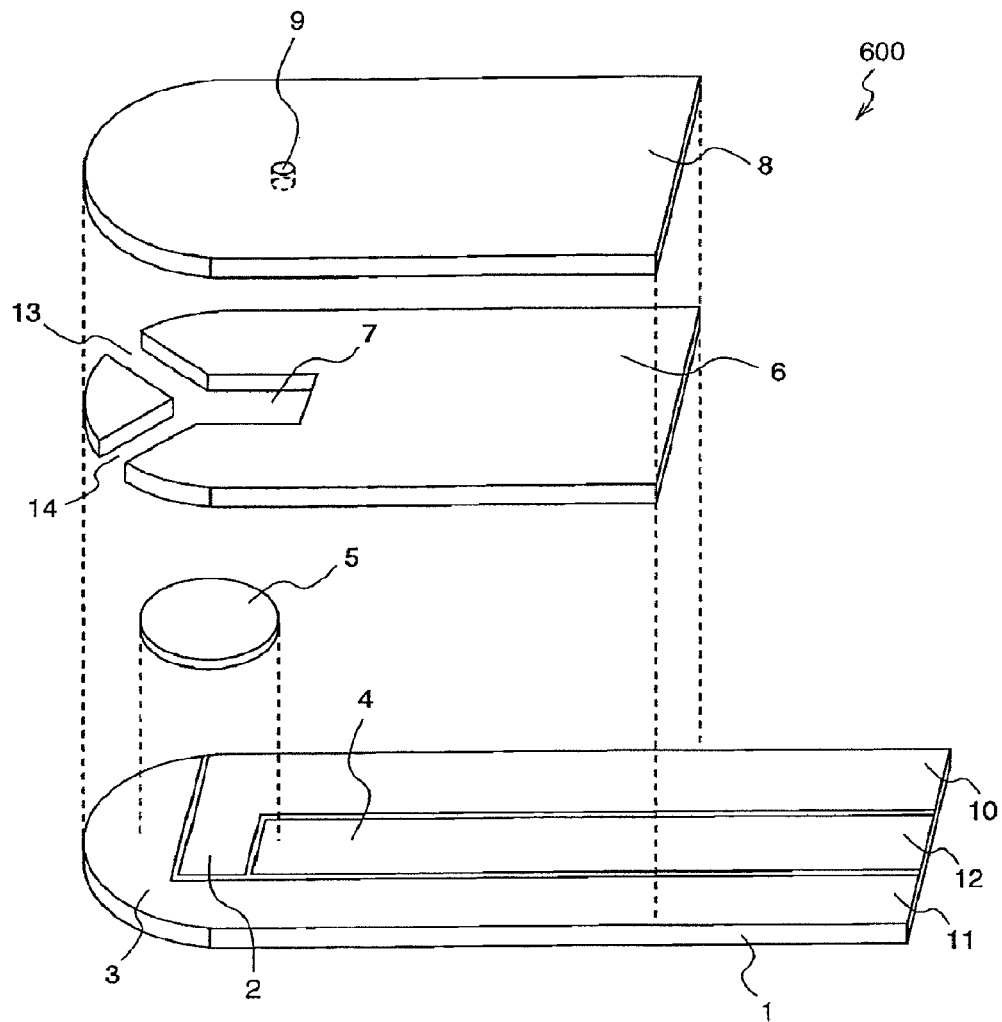
FIG. 6 illustrates an exploded perspective view and a cross-sectional view of a biosensor 600 according to a third embodiment of the present invention.
Figure 6B:
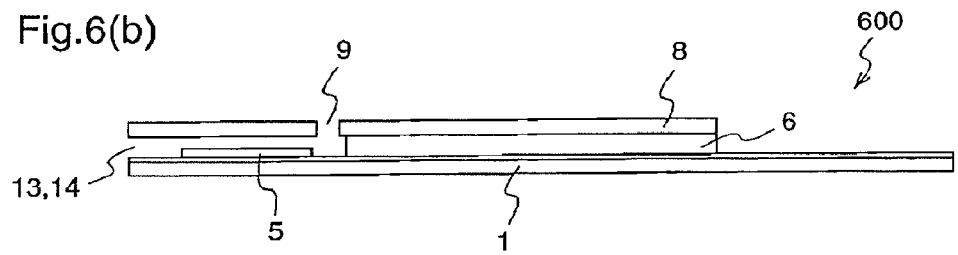

FIG. 6 illustrates an exploded perspective view and a cross-sectional view of a biosensor 600 according to a third embodiment of the present invention.

In the biosensor 600 of the third embodiment shown in FIG. 6, the capillary 7 branches in a Y shape in the vicinity of the front end, and one of the branches serves as the sample supply port 13 while the other serves as the auxiliary sample supply port 14.

In this third embodiment, since the spacer 6 is provided with the two sample supply ports, the same effects as those of the first and second embodiments are achieved. Further, since the sample supply port 13 and the auxiliary sample supply port 14 can be simultaneously patterned in the spacer 6, the number of process steps in the sensor fabrication can be reduced.

Hereinafter, a specific example of the present invention will be described in detail.

A biosensor constituted as mentioned below is used as an example.

After a palladium thin film having a thickness of about 8 nm is formed by sputtering over the entire surface of a first insulating substrate comprising polyethylene terephthalate, slits are partially formed in the thin film by using a YAG laser, thereby separately forming a measurement electrode, a counter electrode, and a detector electrode.

Thereafter, an aqueous solution containing glucose dehydrogenase as an enzyme and potassium ferricyanide as an electron carrier is dropped circularly so as to partially cover the counter electrode and the detector electrode with the measurement electrode being in the center, and then dried, thereby forming a reagent layer. Further, a spacer comprising polyethylene terephthalate and a second insulating substrate also comprising polyethylene terephthalate are bonded onto the first insulating substrate.

A surface-activating treatment is previously applied to the surface of the second insulating substrate on the sample supply port side, and an air hole is formed through the second insulating substrate, and further, an auxiliary sample supply port is formed at a position apart by 0.2 mm from the sample supply port.

The above-mentioned members are bonded together to complete a biosensor having a capillary into which blood is introduced, which has the same construction as that shown in FIG. 1.

a second insulating substrate 8, and a sample supply port 13 and an auxiliary sample supply port formed by the slit 15 are connected ((14)).

Then, 2 μL of blood which is sufficient to completely fill the sample supply port of the biosensor of this example is collected on a fingertip, the finger is pressed against the sample supply port, and the blood aspiration state when the sample supply port is closed up is checked.

Table 1 shows the test results.

TABLE 1

|  | sample |  | area of AUX supply port | number of AUX supply port | result 1 | 2 | 3 | 4 | 5 |
|---|---|---|---|---|---|---|---|---|---|
|  | conventional sensor | (1) | — | 0 | X | X | X | X | X |
| invention sensor | AUX supply port on 2nd insulating substrate | (2) | 0.005 mm² | 1 | Δ | Δ | X | Δ | ○ |
|  |  | (3) | 0.010 mm² | 1 | ○ | ○ | ○ | ○ | ○ |
|  |  | (4) | 0.030 mm² | 1 | ○ | ○ | ○ | ○ | ○ |
|  |  | (5) | 0.100 mm² | 1 | ○ | ○ | ○ | ○ | ○ |
|  |  | (6) | 0.003 mm² | 2 | Δ | Δ | X | Δ | Δ |
|  |  | (7) | 0.05 mm² | 2 | ○ | ○ | ○ | ○ | ○ |
|  |  | (8) | 0.01 mm² | 4 | ○ | ○ | ○ | ○ | ○ |
|  |  | (9) | 0.01 mm² | 9 | ○ | ○ | ○ | ○ | ○ |
|  | rectangular AUX supply port (FIG. 3) | (10) | 0.01 mm² | 1 | ○ | ○ | ○ | ○ | ○ |
|  | AUX supply ports on both insulating substrates (FIG. 5) | (11) | 0.01 mm² | 2 | ○ | ○ | ○ | ○ | ○ |
|  | AUX supply port on 1st insulating substrate | (12) | 0.01 mm² | 1 | ○ | ○ | ○ | ○ | ○ |
|  | Y-shaped capillary (FIG. 6) | (13) | 0.15 mm² | 1 | ○ | ○ | ○ | ○ | ○ |
| comparison sensor | main supply port short-circuited with AUX supply port (FIG. 7) | (14) | 0.010 mm² | 0 | X | X | X | Δ | Δ |

○: Speedily and accurate aspiration is performed even when finger is pressed.
Δ: Aspiration is lowered in speed or stopped halfway when finger is pressed.
X: Aspiration is stopped when finger is pressed.

Figure 7A:
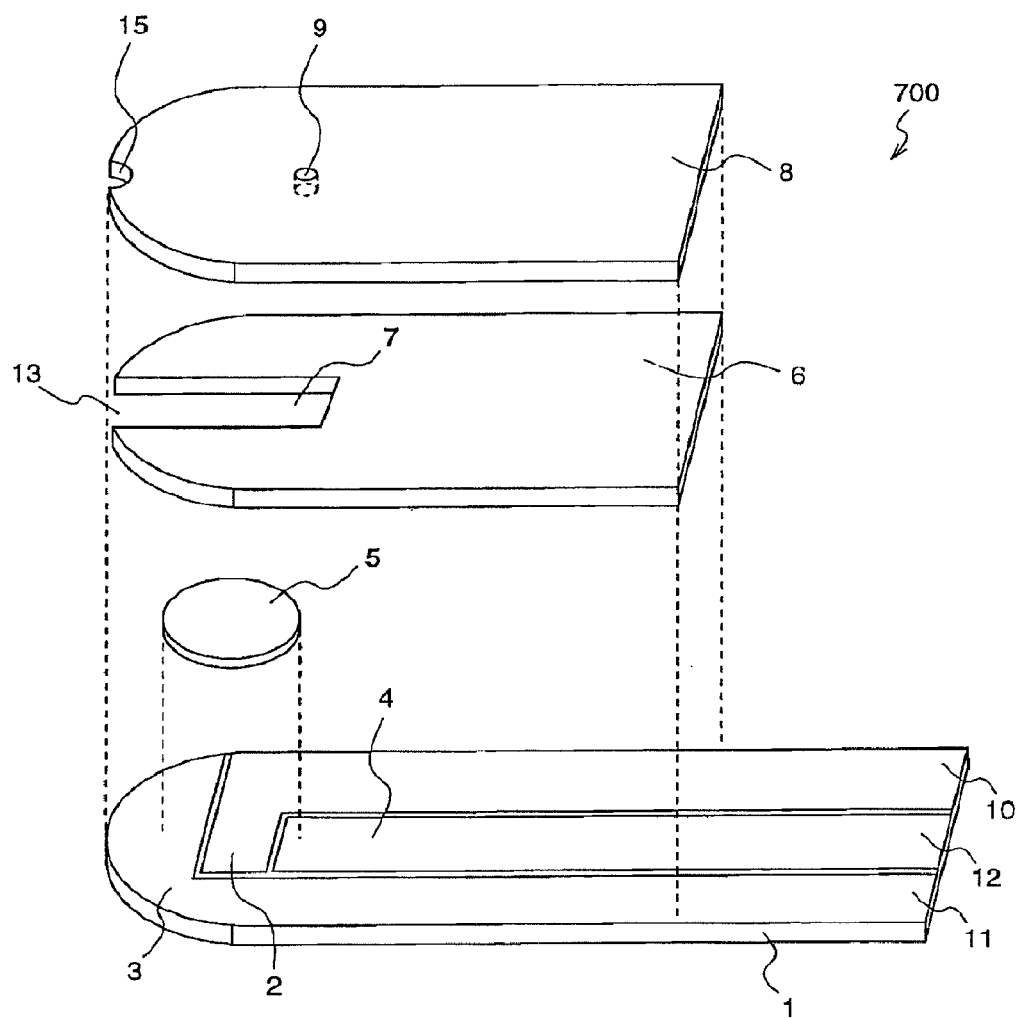
FIG. 7 illustrates an exploded perspective view and a cross-sectional view of a biosensor 700 according to a comparison example of the present invention.
Figure 7B:
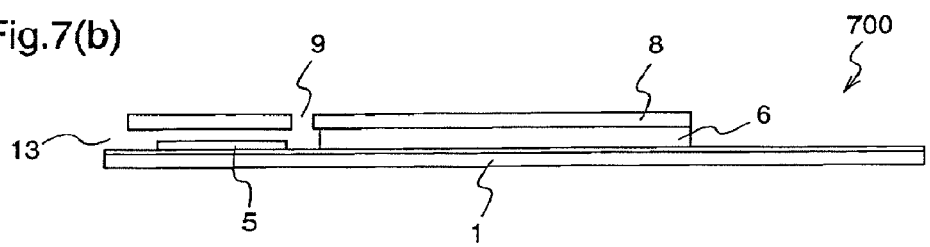
Figure 8A:
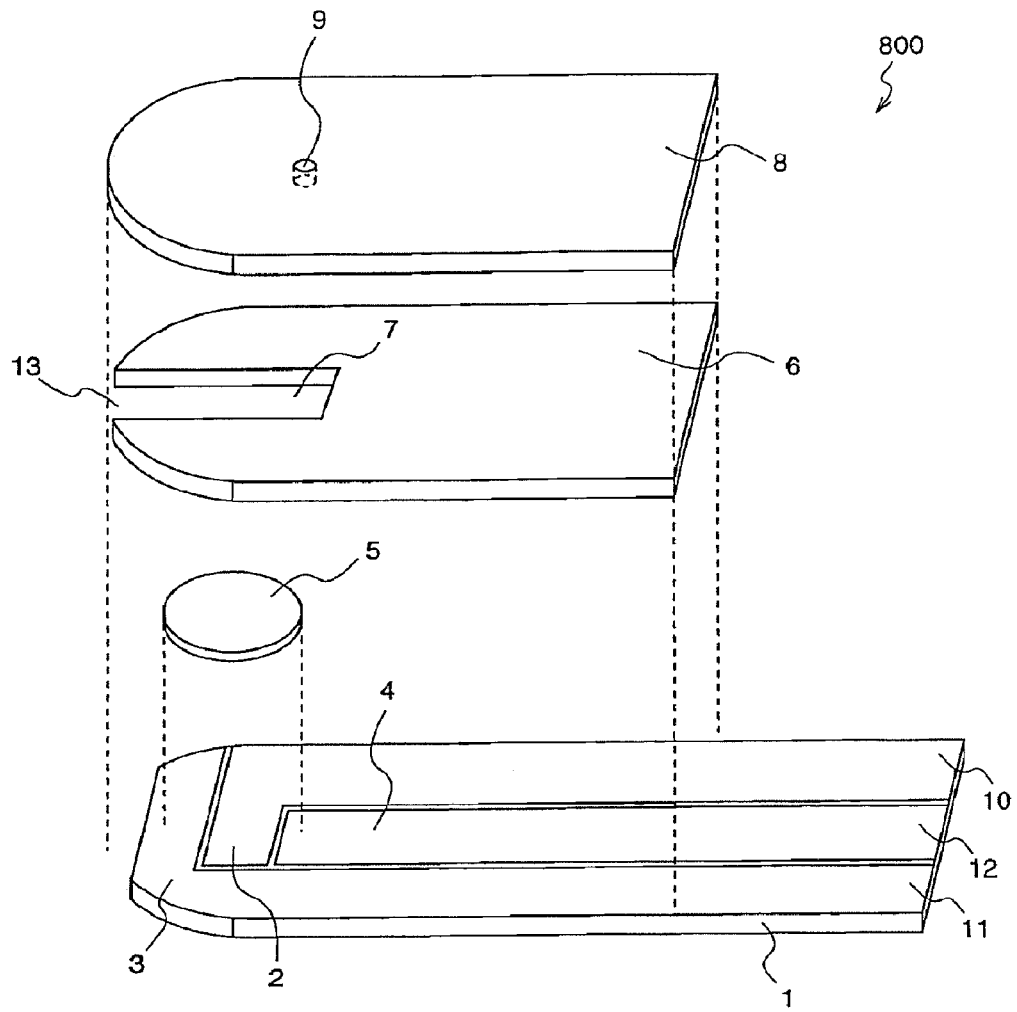
FIG. 8 illustrates an exploded perspective view and a cross-sectional view of the conventional biosensor 800.
Figure 8B:
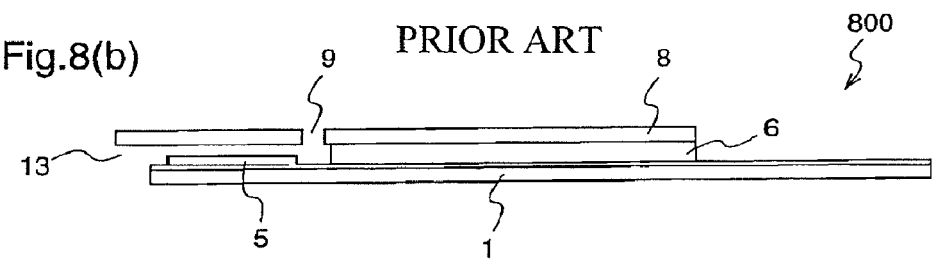
Figure 9A:
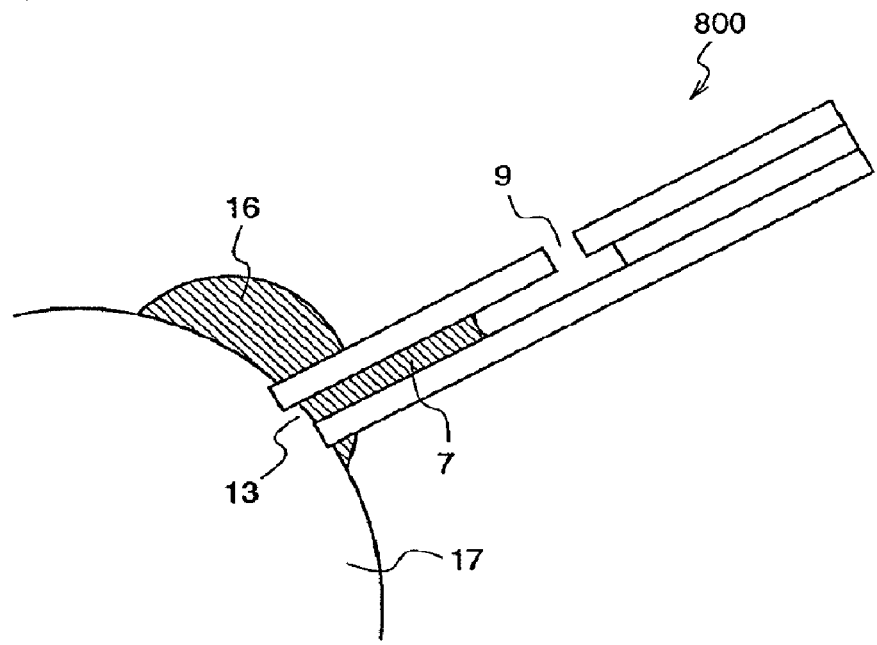
FIG. 9 is a cross-sectional view illustrating a state where blood is aspirated in the conventional biosensor 800.
Figure 9B:
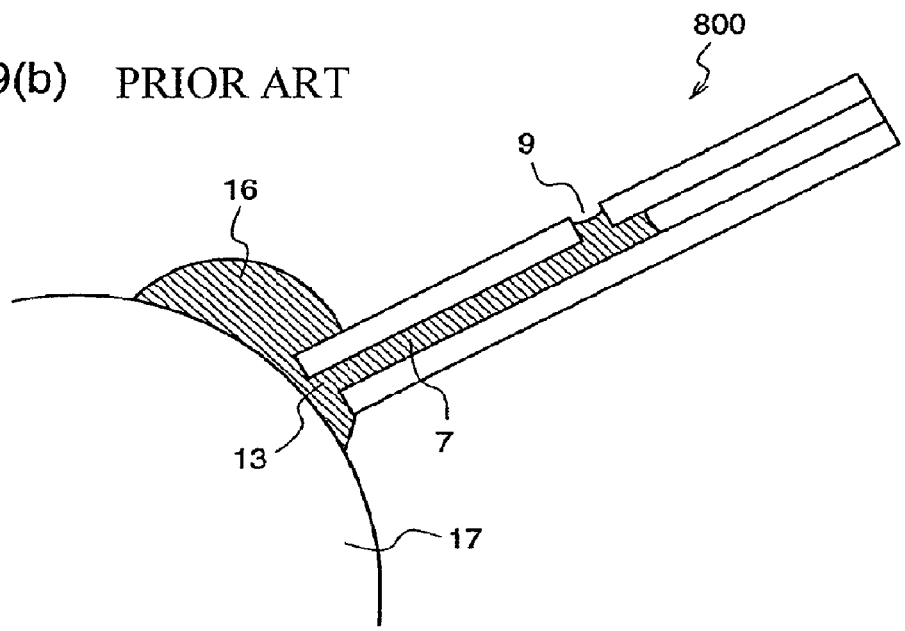

In order to confirm the effects of the present invention, there are fabricated fourteen types of sensors as follows:

a conventional biosensor 800 shown in FIG. 8 ((1));

biosensors 100 according to the first embodiment shown in FIG. 1, wherein the aperture areas of the auxiliary sample supply ports 14 are 0.005 mm², 0.010 mm², 0.030 mm², and 0.100 mm², respectively ((2), (3), (4), (5));

biosensors 200 according to a modification of the first embodiment shown in FIG. 2, wherein the number of the auxiliary sample supply ports 14 is two (area: 0.003 mm²), two (area: 0.050 mm²), four (area: 0.01 mm²), and nine (area: 0.01 mm²), respectively ((6), (7), (8), (9));

a biosensor 300 according to another modification of the first embodiment shown in FIG. 3, wherein the auxiliary sample supply port 14 is rectangle in shape ((10));

a biosensor 500 according to the second embodiment shown in FIG. 5, wherein the auxiliary sample supply ports 14 are formed on both the first insulating substrate 1 and the second insulating substrate 8 ((11));

a biosensor having an auxiliary sample supply port on the first insulating substrate ((12));

a biosensor 600 according to the third embodiment shown in FIG. 6, wherein the capillary 7 is Y-shaped ((13)); and a biosensor 700 as a sensor for comparison shown in FIG. 7, wherein a groove-shaped slit 15 is formed at a front end of As is evident from Table 1, in the conventional biosensor having no auxiliary sample supply port, when the finger is pressed against the sample supply port, aspiration is stopped in all the results. This is because the sample supply port is closed up by pressing an elastic object such as a fingertip, and thereby supply of the sample solution is prevented.

Further, when the area of the auxiliary sample supply port is 0.005 mm², aspiration speed is lowered when the finger is pressed against the supply port. It is estimated that the area of the auxiliary sample supply port is small and insufficient to introduce the blood into the capillary.

When the area of the auxiliary sample supply port is equal to or larger than 0.01 mm², speedily aspiration is carried out even when the finger is pressed against the supply port. It is estimated that even when the sample supply port is closed up and supply of the sample solution is rate-limited, the sample solution is speedily supplied from the auxiliary sample supply port.

When plural auxiliary sample supply ports are provided, the same effects can be obtained so long as the total of the areas of the supply ports is equal to or larger than 0.01 mm².

In the case where the main supply port and the auxiliary supply port are connected and a groove-shaped slit is formed at the front end of the second insulating substrate as shown in FIG. 7, aspiration is stopped or lowered in speed when the finger is pressed against the main supply port, even though the area of the groove is 0.01 mm². It is estimated that when the sample supply port and the auxiliary supply port are connected, the finger pressed against the sample supply port undesirably adheres tightly to the inside of the auxiliary supply port, and thereby the auxiliary supply port becomes incapable of performing its function.

On the other hand, favorable results can be obtained with respect to the biosensor having a rectangle auxiliary sample supply port (refer to FIG. 3), the biosensor having auxiliary sample supply ports on both the first and second insulating substrates 1 and 2 (refer to FIG. 5), the biosensor having an auxiliary sample supply port on the insulating substrate 1, and the biosensor having a Y-shaped capillary (refer to FIG. 6).

When performing measurement with a very small quantity of sample solution as in this example, if the sample supply port and the auxiliary sample supply port are separated by 5 mm or more, it is difficult to make the sample contact these ports simultaneously, and favorable effects cannot be obtained.

Also when the area of the auxiliary sample supply port is equal to or larger than 3 mm², it is difficult to make the sample contact the entirety of the auxiliary supply port for the same reason as mentioned above, and the auxiliary supply port cannot perform its function.

APPLICABILITY IN INDUSTRY

A biosensor according to the present invention is applicable to a blood glucose sensor, a cholesterol sensor, a lactic acid sensor, an alcohol sensor, an amino acid sensor, a fructose sensor, and a sucrose sensor, which collect a very small quantity of sample solution into a capillary and perform analysis. Further, samples used for the analysis may include liquid samples such as blood, urine, sweat, saliva, drinkable water, and sewage water.

The invention claimed is:

1. A biosensor comprising
a first insulating substrate and a second insulating substrate bonded together;
a sample supply port which opens at one end of the bonded insulating substrates, and to which a sample solution is applied;
a capillary communicated with the sample supply port, and into which the applied sample solution is introduced;
an air hole which is positioned at an end of the capillary opposite the sample supply port and communicated with air inside the capillary; and
a spacer having a groove, the spacer being disposed between the first insulating substrate and the second insulating substrate,
wherein said sample supply port and said capillary are formed by bonding the insulating substrates together,
wherein an auxiliary sample supply port communicated with said capillary, through which the applied sample solution is introduced into the capillary, is provided in the vicinity of said sample supply port,
wherein the groove in the spacer forms the capillary and the sample supply port,
wherein the auxiliary sample supply port is disposed at one end of the bonded insulating substrates,
wherein said auxiliary sample supply port is a through-hole penetrating said one of the insulating substrates so as to leave a portion of the insulating substrate between the auxiliary sample supply port and the sample supply port, and is in fluid communication with outer air between the auxiliary sample supply port and the sample supply port, and
wherein an entirety of the capillary between the auxiliary sample supply port and the air hole is covered by said one of the first insulating substrate and the second insulating substrate.

2. A biosensor as defined in claim 1, wherein a total aperture area of said auxiliary sample supply port is 0.01 mm² to 3 mm².

3. A biosensor as defined in claim 1, wherein a distance between said sample supply port and said auxiliary sample supply port is 0.05 to 5 mm.

4. A biosensor as defined in claim 1, wherein said through-hole for the auxiliary sample supply port is fabricated using a laser.

5. A biosensor as defined in claim 1, wherein a surface-activating treatment is applied to at least a portion of a surface of the first insulating substrate or the second insulating substrate, said portion facing the capillary.

6. A biosensor as defined in claim 1, wherein a surface-activating treatment is applied to an inner wall of the auxiliary sample supply port.

7. A biosensor as defined in claim 1, wherein said auxiliary supply port is a first auxiliary supply port, and the biosensor comprises at least on additional auxiliary supply port, and
wherein a total aperture area of the auxiliary sample supply ports is 0.01 mm² to 3 mm².

8. A biosensor as defined in claim 1, wherein said auxiliary sample supply port is disposed between said air hole and said sample supply port.

9. A biosensor as defined in claim 1, wherein said auxiliary supply port is a first auxiliary supply port and the biosensor includes at least one additional auxiliary supply port, and
wherein each of said auxiliary sample supply ports is disposed between said air hole and said sample supply port.

10. A biosensor as defined in claim 1, wherein said auxiliary sample supply port and said air hole are disposed in said second insulating substrate, and
wherein said auxiliary sample supply port is disposed between said air hole and said sample supply port.

11. A biosensor as defined in claim 1, wherein said auxiliary sample supply port is formed in one of said insulating substrates, said sample supply port is formed between said insulating substrates, and said air hole is formed in one of said insulating substrates.

12. A biosensor as defined in claim 1, further comprising a reagent layer disposed between the spacer and the second insulating substrate, the reagent layer being in fluid communication with the capillary.

13. A biosensor as defined in claim 1, wherein electrodes and a reagent layer for electrochemically analyzing a specific substance in the sample solution are provided on a surface of the first insulating substrate or the second insulating substrate, said surface facing the capillary.

14. A biosensor as defined in claim 13, wherein the first insulating substrate and the second insulating substrate have different shapes at an end of the biosensor where the sample supply port is formed.

15. A biosensor as defined in claim 14, wherein the electrodes or the reagent layer are/is not provided on the first or second insulating substrate which is opposed to the auxiliary sample supply port.

* * * * *